(12) United States Patent
Gunderson et al.

(10) Patent No.: US 11,278,728 B2
(45) Date of Patent: Mar. 22, 2022

(54) IDENTIFY INSULATION BREACH USING ELECTROGRAMS

(71) Applicant: Medtronic, Inc., Minneapolis, MN (US)

(72) Inventors: Bruce D. Gunderson, Plymouth, MN (US); Marshall S. Stanton, Orono, MN (US)

(73) Assignee: Medtronic, Inc., Minneapolis, MN (US)

(*) Notice: Subject to any disclaimer, the term of this patent is extended or adjusted under 35 U.S.C. 154(b) by 140 days.

(21) Appl. No.: 16/408,910

(22) Filed: May 10, 2019

(65) Prior Publication Data

US 2019/0262603 A1 Aug. 29, 2019

Related U.S. Application Data

(60) Division of application No. 14/458,502, filed on Aug. 13, 2014, now Pat. No. 10,293,155, which is a continuation-in-part of application No. 13/835,600, filed on Mar. 15, 2013, now Pat. No. 9,008,773.

(60) Provisional application No. 62/019,008, filed on Jun. 30, 2014.

(51) Int. Cl.
*A61N 1/08* (2006.01)
*A61N 1/37* (2006.01)
*A61N 1/39* (2006.01)

(52) U.S. Cl.
CPC ......... *A61N 1/3706* (2013.01); *A61N 1/3925* (2013.01); *A61N 2001/083* (2013.01)

(58) Field of Classification Search
CPC ............... A61N 1/3706; A61N 1/3925; A61N 2001/083

USPC ....................................................... 600/509
See application file for complete search history.

(56) References Cited

U.S. PATENT DOCUMENTS

| | | | |
|---|---|---|---|
| 3,602,215 | A | 8/1971 | Parnell |
| 5,344,430 | A | 9/1994 | Berg et al. |
| 5,354,316 | A | 10/1994 | Keimel |
| 5,455,186 | A | 10/1995 | Inn |
| 5,549,646 | A | 8/1996 | Katz et al. |
| 5,593,431 | A | 1/1997 | Sheldon |
| 5,755,742 | A | 5/1998 | Schuelke et al. |
| 5,776,168 | A | 7/1998 | Gunderson |

(Continued)

FOREIGN PATENT DOCUMENTS

| | | | |
|---|---|---|---|
| CN | 102458572 A | 5/2012 | |
| CN | 104168949 A | 3/2013 | |

(Continued)

OTHER PUBLICATIONS

Leong et al., "Unrecognized Failure of a Narrow Caliber Defibrillation Lead: The Role of Defibrillation Threshold Testing in Identifying an Unprotected Individual", PACE, vol. 00, 2012, 2 pages.

(Continued)

*Primary Examiner* — Erin M Piateski
(74) *Attorney, Agent, or Firm* — Shumaker & Sieffert, P.A.

(57) ABSTRACT

An implantable medical device capable of sensing cardiac signals and delivering cardiac electrical stimulation therapies is enabled to detect a short circuit event. A signal is sensed by a sensing module coupled to electrodes. A controller detects a short circuit event in response to a slope of the sensed signal exceeding a short circuit threshold.

20 Claims, 10 Drawing Sheets

(56) References Cited

U.S. PATENT DOCUMENTS

| | | | |
|---|---|---|---|
| 5,814,088 A | 9/1998 | Paul et al. | |
| 5,897,577 A | 4/1999 | Cinbis et al. | |
| 5,957,861 A | 9/1999 | Combs et al. | |
| 5,959,861 A | 9/1999 | Kaneko | |
| 6,393,316 B1 | 5/2002 | Gillberg et al. | |
| 6,599,242 B1 * | 7/2003 | Splett | A61B 5/0006 345/440.1 |
| 7,047,083 B2 | 5/2006 | Gunderson et al. | |
| 7,120,493 B2 | 10/2006 | Propp et al. | |
| 7,242,978 B2 | 7/2007 | Cao et al. | |
| 7,266,409 B2 | 9/2007 | Gunderson | |
| 7,277,757 B2 | 10/2007 | Casavant et al. | |
| 7,289,851 B2 | 10/2007 | Gunderson et al. | |
| 7,454,249 B1 | 11/2008 | Bornzin et al. | |
| 7,515,961 B2 | 4/2009 | Germanson et al. | |
| 7,747,320 B1 | 6/2010 | Kroll et al. | |
| 7,783,354 B2 | 8/2010 | Gunderson | |
| 7,974,690 B2 | 7/2011 | Kracker | |
| 8,099,166 B2 | 1/2012 | Schüller et al. | |
| 8,200,322 B2 | 6/2012 | Ousdigian et al. | |
| 8,200,330 B2 | 6/2012 | Kroll et al. | |
| 8,355,783 B2 | 1/2013 | Goetz et al. | |
| 8,391,979 B2 | 3/2013 | Kuhn et al. | |
| 8,396,543 B2 | 3/2013 | Hoeppner et al. | |
| 8,401,629 B2 | 3/2013 | Stadler et al. | |
| 8,543,206 B2 | 9/2013 | Naware et al. | |
| 8,626,293 B2 | 1/2014 | Bornzin et al. | |
| 8,738,111 B2 | 5/2014 | Sweeney et al. | |
| 9,008,773 B2 | 4/2015 | Gunderson | |
| 9,199,078 B1 | 12/2015 | Gunderson | |
| 9,220,901 B2 | 12/2015 | Gururaj et al. | |
| 2002/0120307 A1 * | 8/2002 | Jorgenson | A61N 1/3925 607/27 |
| 2004/0064161 A1 | 4/2004 | Gunderson et al. | |
| 2005/0137636 A1 | 6/2005 | Gunderson et al. | |
| 2006/0116733 A1 | 6/2006 | Gunderson | |
| 2006/0235476 A1 | 10/2006 | Gunderson et al. | |
| 2006/0264777 A1 | 11/2006 | Drew | |
| 2007/0100407 A1 | 5/2007 | Armstrong | |
| 2007/0293903 A1 | 12/2007 | Bohn et al. | |
| 2008/0161870 A1 | 7/2008 | Gunderson | |
| 2008/0161872 A1 | 7/2008 | Gunderson | |
| 2008/0215110 A1 | 9/2008 | Gunderson | |
| 2009/0270938 A1 | 10/2009 | Pei et al. | |
| 2009/0299422 A1 | 12/2009 | Ousdigian et al. | |
| 2010/0023084 A1 | 1/2010 | Gunderson | |
| 2010/0106209 A1 | 4/2010 | Gunderson et al. | |
| 2010/0114222 A1 | 5/2010 | Gunderson et al. | |
| 2010/0228307 A1 | 9/2010 | Kroll et al. | |
| 2010/0286542 A1 * | 11/2010 | India | A61B 5/0452 600/521 |
| 2010/0318149 A1 | 12/2010 | Kuhn et al. | |
| 2011/0009918 A1 | 1/2011 | Bornzin et al. | |
| 2011/0054558 A1 | 3/2011 | Gunderson et al. | |
| 2011/0098766 A1 | 4/2011 | Gunderson | |
| 2011/0184481 A1 | 7/2011 | Hoeppner et al. | |
| 2011/0319957 A1 | 12/2011 | Naware et al. | |
| 2012/0004699 A1 | 1/2012 | Bobgan et al. | |
| 2012/0109235 A1 | 5/2012 | Sheldon et al. | |
| 2012/0143278 A1 | 6/2012 | Ryu et al. | |
| 2012/0158089 A1 | 6/2012 | Bocek et al. | |
| 2012/0179056 A1 | 7/2012 | Moulder et al. | |
| 2012/0191153 A1 | 7/2012 | Swerdlow et al. | |
| 2013/0013038 A1 | 1/2013 | Miller | |
| 2013/0253352 A1 * | 9/2013 | Bornzin | G01R 31/00 600/509 |
| 2014/0018873 A1 | 1/2014 | Gunderson | |

FOREIGN PATENT DOCUMENTS

| | | |
|---|---|---|
| WO | 2006119136 A1 | 11/2006 |
| WO | 2010123895 A2 | 10/2010 |

OTHER PUBLICATIONS

Gunderson et al., "Identify Insulation Breach Using Electrograms", Notice of First Office Action for Chinese Application No. 201580035649.X, dated Oct. 15, 2018, 7 pages.

Gunderson et al., "Identify Insulation Breach Using Electrograms", Notice of First Office Action for Chinese Application No. 201580035546.3, dated Aug. 10, 2018, 12 pages.

(PCT/US2015/036541) PCT Notification of Transmittal of the International Search Report and the Written Opinion of the International Searching Authority, dated Feb. 10, 2016, 11 pages.

* cited by examiner

IDENTIFY INSULATION BREACH USING ELECTROGRAMS

CROSS REFERENCE TO RELATED APPLICATIONS

This application is a Division of U.S. patent application Ser. No. 14/458,502, filed Aug. 13, 2014, entitled "IDENTIFY INSULATION BREACH USING ELECTROGRAMS," which was a continuation-in-part of U.S. patent application Ser. No. 13/835,600, filed Mar. 15, 2013, entitled "IDENTIFICATION OF INSULATION BREACH USING ELECTROGRAMS," (granted as U.S. Pat. No. 9,008,773) and which also claims the benefit of the filing date of U.S. Provisional Application No. 62/019,008, filed on Jun. 30, 2014, entitled "IDENTIFY INSULATION BREACH USING ELECTROGRAMS." The content of all of which is incorporated herein by reference in their entirety.

FIELD OF THE DISCLOSURE

The disclosure relates generally to medical devices configured to deliver electrical therapies. In particular, the disclosure relates to devices and methods for detecting a medical electrical lead insulation breach using electrograms.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter defibrillators (ICDs), provide therapeutic electrical stimulation to or monitor the heart of the patient via electrodes carried by one or more implantable leads. The leads may be transvenous, i.e., implanted in the heart through one or more veins. Other leads may be non-transvenous leads implanted outside the heart and blood vessels. In either case, the electrical stimulation provided by the IMD may include signals such as pacing pulses, cardioversion shocks or defibrillation shocks to address abnormal cardiac rhythms such as bradycardia, tachycardia or fibrillation.

ICDs typically have the capability of delivering both low voltage therapies and high voltage therapies in response to monitoring a cardiac rhythm and detecting a need for therapy. Low voltage therapies may include bradycardia pacing, cardiac resynchronization therapy (CRT), and anti-tachycardia pacing (ATP). Low voltage therapies are typically delivered using low voltage pacing electrodes, e.g., tip or ring electrodes delivering pulses of 5 Volts or less in amplitude.

High voltage therapies such as cardioversion or defibrillation shocks are delivered in response to detecting ventricular tachycardia or ventricular fibrillation. High voltage therapies are typically delivered using high voltage coil electrodes and the housing of the ICD, often referred to as the "CAN electrode" or a "housing electrode." High voltage electrodes generally have a greater surface area than low voltage electrodes and deliver high energy shock pulses, typically in the range of at least 10 Joules and up to 35 Joules for transvenous lead systems carrying intracardiac defibrillation electrodes and in the range of at least 65 Joules and up to 80 Joules for subcutaneous lead systems carrying extracardiac defibrillation electrodes.

A single lead coupled to an ICD may carry multiple electrodes, which may include either or both high voltage and low voltage electrodes. Each electrode is coupled to an electrically insulated conductor extending through the elongated lead body to facilitate electrical connection of each therapy delivery electrode to pulse generating circuitry within the ICD.

SUMMARY

In general, the disclosure is directed to techniques for detecting a short circuit condition of an implantable medical electrical lead. An ICD operating in accordance with the techniques performs cardiac electrical signal analysis for detecting short circuit events.

In one example, the disclosure provides an implantable medical device (IMD) system comprising at least one medical electrical lead and an implantable medical device adapted to be coupled to the at least one medical electrical lead. The medical electrical lead includes a plurality of electrodes carried by the medical electrical lead and a plurality of electrical conductors, each of the plurality of electrical conductors electrically connected to a respective one of the plurality of electrodes. The IMD includes a sensing module electrically coupled to the plurality of electrical conductors when the IMD is electrically coupled to the at least one medical electrical lead and a controller electrically coupled to the sensing module. The sensing module is configured to sense a cardiac signal using at least one of the plurality of electrodes. The controller is configured to receive the cardiac signal, determine a slope of the cardiac signal, compare the slope of the cardiac signal to a short circuit threshold, and detect a short circuit event within the medical electrical lead when the slope of the cardiac signal exceeds the short circuit threshold.

In another example, the disclosure provides a method comprising sensing a cardiac signal via a plurality of electrodes carried by an implantable medical electrical lead, determining a slope of the cardiac signal, comparing the slope of the cardiac signal to a short circuit threshold; and detecting a short circuit event within the implantable medical electrical lead when the slope of the cardiac signal exceeds a short circuit threshold.

In another example, the disclosure provides a computer-readable storage medium comprising instructions that, when executed by a controller in an IMD, cause the IMD to sense a cardiac signal via a plurality of electrodes carried by an implantable medical electrical lead, determine a slope of the cardiac signal, compare the slope of the cardiac signal to a short circuit threshold; and detect a short circuit event within the implantable medical electrical lead when the slope of the cardiac signal exceeds a short circuit threshold.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for detecting a short circuit condition of a medical electrical lead in an IMD system. A short circuit condition of a medical electrical lead can sometimes occur when an electrode or its conductor makes electrical contact with another conductor or electrode of an IMD system. A short circuit that occurs during delivery of a therapy, such as a defibrillation shock, is likely to prevent adequate energy from being delivered to the heart, leading to a failed therapy. Since ventricular fibrillation is a life-threatening condition, prompt detection of a potential short circuit condition involving the high voltage electrodes or conductors is needed. Lead impedance measurements may be performed on a regular basis to monitor for possible short-circuit, open-circuit or other lead conditions. However, since a short circuit condition may be an intermittent or sporadic condition, scheduled lead impedance measurements may not always detect a short circuit condition.

An ICD according to the present disclosure includes a controller that is configured to receive a cardiac electrical signal, such as an intracardiac electrogram (EGM) signal via intracardiac electrodes, or an electrocardiogram (ECG) signal received via electrodes implanted outside the cardiovascular system. The controller is configured to detect a short circuit condition based on an analysis of the cardiac electrical signal.

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
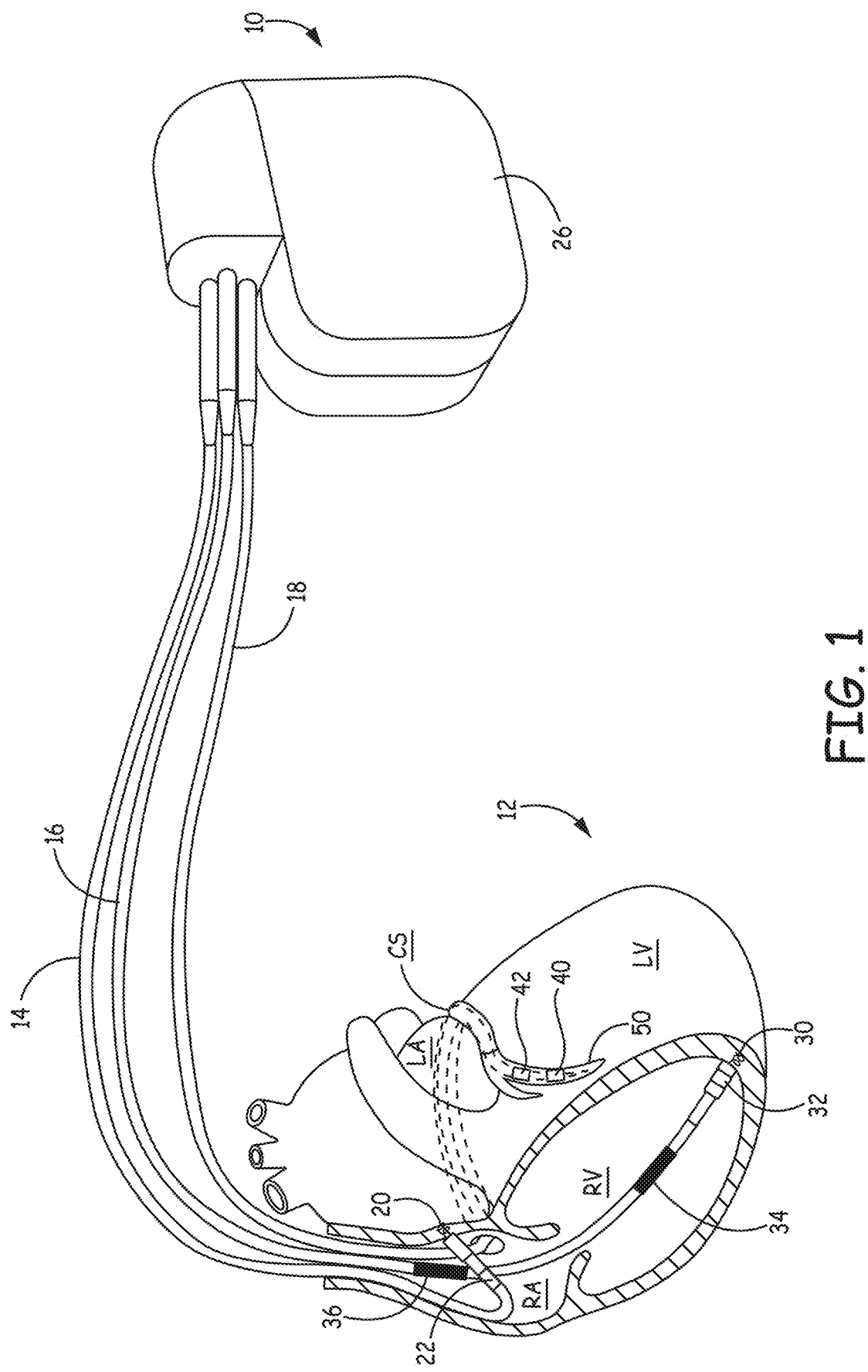
FIG. 1 is a schematic representation of an implantable medical device system including an implantable medical device (IMD) capable of delivering high voltage and low voltage therapies to a heart via one or more implantable medical leads.

FIG. 1 is a schematic representation of an implantable medical device system 2 that includes an implantable medical device (IMD) 10 capable of delivering high voltage and low voltage therapies to heart 12. IMD 10 is coupled to heart 12 via leads 14, 16 and 18. Right atrial lead 14 extends from IMD 10 to the right atrium (RA) and carries distal electrodes 20 and 22 for sensing cardiac electrical signals and delivering pacing pulses in the RA. In addition, a housing electrode 26, also referred to as a CAN electrode, can be formed as part of the or the entire outer surface of the housing of IMD 10 and be used as an active electrode in combination with electrodes 20 and/or 22 to deliver the pacing pulses in the RA.

Right ventricular lead 16 carries a tip electrode 30 and a ring electrode 32 for sensing cardiac electrical signals and delivering pacing pulses in the RV. RV lead 16 additionally carries high voltage coil electrodes 34 and 36, referred to herein as the RV coil electrode 34 and the superior vena cava (SVC) coil electrode 36, for delivering high voltage cardioversion and defibrillation shocks in response to detecting a shockable tachyarrhythmia from sensed cardiac signals. In addition, housing or CAN electrode 26 may be used with pace/sense electrodes 30 and 32 for delivering RV pacing pulses or as an active electrode in combination with coil electrodes 34 and/or 36 during shock delivery.

A coronary sinus (CS) lead 18 is shown extending into a cardiac vein 50 via the RA and coronary sinus for positioning electrodes 40 and 42 for sensing cardiac signals and delivering pacing pulses along the left ventricle. In some examples, CS lead 18 may additionally carry electrodes for positioning along the left atrium for sensing and stimulation along the left atrial chamber. Moreover, CS lead 18 may carry additional electrodes positioned along the left ventricle, e.g., four electrodes. In addition, housing or CAN electrode 26 may be used as an electrode in combination with electrodes 40 and/or 42 to deliver the pacing pulses to the LV.

The depicted positions in or about the right and left heart chambers are merely illustrative. Other leads and pace/sense electrodes and/or high voltage electrodes can be used instead of, or in combination with, any one or more of the depicted leads and electrodes shown in FIG. 1. Lead and electrode configurations are not limited to transvenous leads and intravenous or intracardiac electrodes as shown in FIG. 1. In some embodiments, an IMD system may include subcutaneous electrodes, which may be carried by an extravenous lead extending from IMD 10 subcutaneously outside the ribcage and sternum, or substernal electrodes, which may be carried by an extravenous lead having a distal end extending underneath the sternum and/or ribcage (e.g., along the posterior side of the sternum).

IMD 10 is shown as a multi-chamber device capable of sensing and stimulation in three or all four heart chambers. It is understood that IMD 10 may be modified to operate as a single chamber device, e.g. with a lead positioned in the RV only, or a dual chamber device, e.g. with a lead positioned in the RA and a lead positioned in the RV. In general, IMD 10 may be embodied as any single, dual or multi-chamber device including lead and electrode systems for delivering at least a high voltage therapy and may be configured for delivering both high voltage shock pulses and low voltage pacing pulses.

Figure 2:
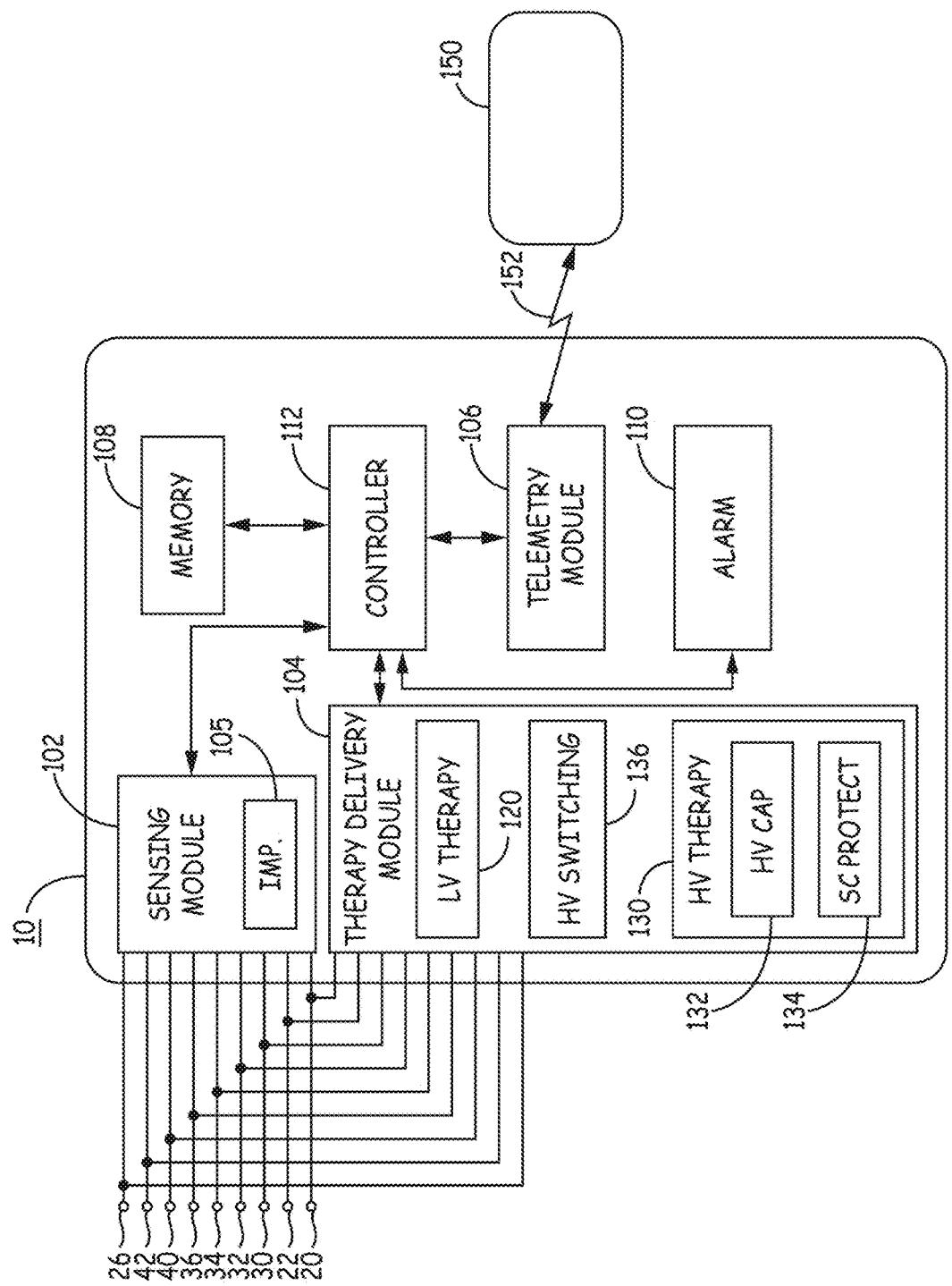
FIG. 2 is a functional block diagram of the IMD shown in FIG. 1 according to an illustrative embodiment.

FIG. 2 is a functional block diagram of the IMD 10 shown in FIG. 1 according to an illustrative embodiment. IMD 10 includes a sensing module 102, a therapy delivery module 104, a telemetry module 106, memory 108, and a control unit 112, also referred to herein as "controller" 112.

Sensing module 102 is coupled to electrodes 20, 22, 30, 32, 34, 36, 40, 42 and housing electrode 26 (all shown in FIG. 1) for sensing EGM signals. Sensing module 102 monitors cardiac electrical signals for sensing signals attendant to the depolarization of myocardial tissue, e.g., P-waves and R-waves, from selected ones of electrodes 20, 22, 26, 30, 32, 34, 36, 40, and 42 in order to monitor electrical activity of heart 12. Sensing module 102 may include a switch module to select which of the available electrodes are used to sense the cardiac electrical activity. The switch module may include a switch array, switch matrix, multiplexer, or any other type of switching device suitable to selectively couple electrodes to sensing module 102. In some examples, controller 112 selects the electrodes to function as sense electrodes, or the sensing vector, via the switch module within sensing module 102.

Sensing module 102 may include multiple sensing channels, each of which may be selectively coupled to respective combinations of electrodes 20, 22, 26, 30, 32, 34, 36, 40, and 42 to detect electrical activity of a particular chamber of heart 12, e.g. an atrial sensing channel and a ventricular sensing channel. Each sensing channel may comprise an amplifier that outputs an indication to controller 112 in response to sensing a cardiac signal attendant to cardiac depolarization in a respective chamber of heart 12. In this manner, controller 112 may receive sense event signals corresponding to the occurrence of R-waves and P-waves in the various chambers of heart 12. Sensing module 102 may further include digital signal processing circuitry for providing controller 112 with digitized EGM signals, which may be used to determine EGM signal features or for signal morphology analysis in some embodiments. To this end, sensing module 102 may digitize the cardiac signal into multi-bit digital signals defining sequential sample points, e.g., using an analog-to-digital converter (ADC) or other circuitry.

Different sensing channels may additionally or alternatively be coupled to various electrode combinations for providing both near field (NF) sensing vectors and far field (FF) sensing vectors. As used herein, a FF signal is a signal that is obtained using an electrode pair that includes electrodes that are not located in the same heart chamber. For example, at least one electrode is located outside the heart chamber for which events are being sensed, in either a different heart chamber or even outside the heart. A NF signal is a signal that is obtained using a pair of sensing electrodes that are both located in the same heart chamber for which events are being sensed. For example, a NF sensing vector may be sensed between RV tip electrode 30 and RV ring electrode 32 for sensing ventricular R-waves. A FF sensing vector may be sensed between RV coil electrode 34 and SVC coil electrode 36, located outside the ventricles, for sensing ventricular R-waves.

Sensing module 102 and controller 112 are configured to monitor the patient's cardiac rhythm for determining a need for therapy delivery and for timing therapy delivery. In response to detecting a tachyarrhythmia, controller 112 controls therapy delivery module 104 to deliver a therapy according to programmed therapies stored in memory 108.

Sensing module 102 may include impedance monitoring circuitry 105 for measuring current between a measurement pair of electrodes 20, 22, 30, 32, 34, 36, 40, 42 and housing electrode 26 in response to a drive signal. The drive signal is generally a low voltage signal, and impedance measurements may be used by control 112 to detect short circuit conditions or other lead-related issues detectable when a low voltage drive signal is used. Such low voltage impedance measurements may be performed periodically or in response to loss of pacing capture or a change in pacing threshold to detect lead-related issues. As will be described herein, impedance monitoring may be controlled and adjusted to promote the identification of a short circuit condition, as evidenced by a decrease in impedance.

Sensing module 102 provides controller 112 digitized EGM signals for detecting a possible insulation breach and short circuit condition in some embodiments. As further described below, controller 112 includes processing circuitry for analyzing the EGM signal to detect a signature noise waveform that is characteristic of a short circuit condition. In particular, a high priority is given to monitoring for a short circuit condition that could lead to shorting of a HV shock delivered to treat a malignant tachyarrhythmia. Real-time monitoring for a short circuit condition is described herein. It is contemplated, however, that identification of a short circuit condition may be performed during post processing. An epoch of data (e.g., 10 sec) could be stored at regular intervals in the memory 108 or triggered storage based on a detected event. The data may be post-processed either within IMD 10 or external device 150.

Therapy delivery module 104 is coupled to electrodes 20, 22, 26, 30, 32, 34, 36, 40, and 42 for delivering electrical stimulation therapy to the patient's heart. In some embodiments, therapy delivery module 104 includes low voltage (LV) therapy circuitry 120 including a pulse generator for generating and delivering LV pacing pulses during bradycardia pacing, cardiac resynchronization therapy (CRT), and anti-tachycardia pacing (ATP). Controller 112 controls LV therapy circuitry 120 to deliver pacing pulses according to programmed control parameters using pacing electrodes 20, 22, 30, 32, 40 and/or 42 for example. Electrodes 20, 22, 30 32, 40 and 42 are generally referred to as "low voltage" electrodes because they are normally used for delivering relatively low voltage therapies such as pacing therapies as compared to the high voltage therapies, i.e., cardioversion and defibrillation therapies, delivered by high voltage coil electrodes 32 and 34. However, in some instances LV electrodes 20, 22, 30, 32 40 and 42 may be used for delivering a high voltage therapy in response to detection of a high voltage short circuit condition.

Therapy delivery module 104 includes high voltage (HV) therapy delivery circuitry 130 for generating and delivering high voltage cardioversion and defibrillation shock pulses. HV therapy delivery circuitry 130 includes HV capacitors 132 that are charged in response to detecting a shockable cardiac rhythm, e.g., a ventricular tachycardia or ventricular fibrillation. After determining HV capacitors 132 have reached a targeted voltage, according to a programmed shock energy, HV therapy delivery 130 delivers a shock pulse via selected HV electrodes, e.g., coil electrodes 34, 36 and housing electrode 26.

HV therapy circuitry 130 includes short circuit (SC) protection circuitry for protecting IMD 10 against a short circuit fault during HV therapy delivery. In one embodiment, SC protection circuitry 134 monitors the current during the shock pulse delivery and in response to a relatively high current, e.g., very low impedance, SC protection circuitry 134 immediately terminates the shock pulse, e.g., by an electronic switch, to prevent damage to the circuitry of IMD 10. The HV short circuit condition would prevent delivery of the HV shock to the heart and would fail to terminate a detected shockable rhythm. By protecting the IMD circuitry from the SC fault, controller 112 remains operable to alter the HV therapy delivery to still treat the tachyarrhythmia and/or control therapy delivery module 104 to deliver alternative electrical stimulation therapies.

In response to identifying a short circuit condition, controller 112 may store in memory 108 an electrode vector and polarity combination being used that provided evidence of a short circuit condition. This information may be retrieved and used by a clinician in resolving the short circuit condition, e.g. by replacing a lead or reprogramming the therapy delivery electrode configuration and polarity. This information may be used by controller 112 in selecting electrode vectors and polarities for delivering future HV and/or LV therapies.

Therapy delivery module 104 includes HV switching circuitry 136 used for controlling the pathway through which HV capacitors 132 are discharged. HV switching circuitry 136 may include a switch array, switch matrix, multiplexer, or any other type of switching device suitable to selectively couple combinations of low voltage electrodes (e.g., electrodes 20, 22, 30, 32, 40 and 42) and/or high voltage electrodes (e.g., electrodes 34 and 36) and housing electrode 26 to HV therapy circuitry 130. In some examples, controller 112 selects a shock vector using any of HV coil electrodes 34, 36 and housing electrode 26. As will be described below, controller 112 may select the polarity of the electrodes included in the shock vector using switching circuitry 136.

In some embodiments, the HV capacitors may be coupled to multiple pacing electrode cathodes simultaneously, e.g., any combination or all of LV electrodes 20, 22, 30, 32, 40 and 42 for delivering a HV shock in response to a HV short circuit condition. The anode may be any of the coil electrodes 34, 36, housing electrode 26 or combination of remaining LV electrodes 20, 22, 30, 32, 40 and 42 or any other housing based or lead based electrodes that may be available in the particular IMD system. Pacing capacitors coupled to electrodes 20, 22, 30, 32, 40 and 42 included in LV therapy circuitry 120 may be used in distributing the HV charge remaining on the HV capacitor(s) 132 in some embodiments in an attempt to deliver a needed shock therapy. In this case the pacing capacitors are rated for adequately high voltage to distribute the shock energy among selected electrodes.

Controller 112 may be embodied as a processor including any one or more of a microprocessor, a digital signal processor (DSP), an application specific integrated circuit (ASIC), a field-programmable gate array (FPGA), or equivalent discrete or integrated logic circuitry. In some examples, controller 112 may include multiple components, such as any combination of one or more microprocessors, one or more controllers, one or more DSPs, one or more ASICs, or one or more FPGAs, as well as other discrete or integrated logic circuitry. The functions attributed to controller 112 herein may be embodied as software, firmware, hardware or any combination thereof. Controller 112 includes a therapy control unit that controls therapy module 104 to deliver therapies to heart 12 according to a selected one or more therapy programs, which may be stored in memory 108. Controller 112 and associated memory 108 are coupled to the various components of IMD 10 via a data/address bus.

Memory 108 stores intervals, counters, or other data used by controller 112 to control sensing module 102, therapy delivery module 104 and telemetry module 106. Such data may include intervals and counters used by controller 112 for detecting a heart rhythm and to control the delivery of therapeutic pulses to heart 12. Memory 108 also stores intervals for controlling cardiac sensing functions such as blanking intervals and refractory sensing intervals. Events (P-waves and R-waves) sensed by sensing module 102 may be identified based on their occurrence outside a blanking interval and inside or outside of a refractory sensing interval.

Memory 108 may store computer-readable instructions that, when executed by controller 112, cause IMD 10 to perform various functions attributed throughout this disclosure to IMD 10. The computer-readable instructions may be encoded within memory 108. Memory 108 may comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, with the sole exception being a transitory propagating signal.

Tachyarrhythmia detection algorithms may be stored in memory 108 and executed by controller 112 for detecting ventricular tachycardia (VT), ventricular fibrillation (VF) as well as discriminating such ventricular tachyarrhythmias, generally referred to herein as "shockable rhythms" from atrial or supraventricular tacharrhythmias, such as sinus tachycardia and atrial fibrillation (A FIB). Ventricular event intervals (R-R intervals) sensed from the EGM signals are commonly used for detecting cardiac rhythms. Additional information obtained such as R-wave morphology, slew rate, other event intervals (e.g., P-P intervals and P-R intervals) or other sensor signal information may be used in detecting, confirming or discriminating an arrhythmia. Reference is made to commonly-assigned U.S. Pat. No. 5,354,316 (Keimel), U.S. Pat. No. 5,545,186 (Olson et al.), U.S. Pat. No. 6,393,316 (Gillberg et al.), and U.S. Pat. No. 8,401,629 (Stadler et al.) for examples of arrhythmia detection and discrimination using EGM signals, all of which patents are incorporated herein by reference in their entirety. The techniques described herein for detecting a short circuit condition and responding thereto may be implemented in the types of devices disclosed in the above-referenced patents.

In response to detecting a shockable rhythm, a programmed therapy is delivered by therapy delivery module 104 under the control of controller 112. A description of high-voltage output circuitry and control of high-voltage shock pulse delivery is provided in the above-incorporated '186 Olson patent. Typically, a tiered menu of arrhythmia therapies are programmed into the device ahead of time by the physician and stored in memory 108. For example, on initial detection of a ventricular tachycardia, an anti-tachycardia pacing therapy may be selected and delivered. On redetection of the ventricular tachycardia, a more aggressive anti-tachycardia pacing therapy may be scheduled. If repeated attempts at anti-tachycardia pacing therapies fail, a HV cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold.

In the event that ventricular fibrillation is identified or the anti-tachycardia pacing is not effective, subsequent therapies may be delivery of one or more HV defibrillation shock pulses, typically in excess of 5 Joules, and more typically in the range of 20 to 35 Joules. Lower energy levels may be employed for cardioversion. In the absence of a HV short circuit condition, the defibrillation pulse energy may be increased in response to failure of an initial pulse or pulses to terminate fibrillation.

IMD 10 may additionally be coupled to one or more physiological sensors 114. Physiological sensors may include pressure sensors, accelerometers, flow sensors, blood chemistry sensors, acoustical sensors, activity sensors or other physiological sensors known for use with implantable cardiac stimulation devices. Physiological sensors may be carried by leads extending from IMD 10 or incorporated in or on the IMD housing. Sensor signals may be used in conjunction with EGM signals for detecting and/or confirming a heart rhythm.

Telemetry module 106 is used for transmitting data accumulated by IMD 10 wirelessly to an external device 150, such as a programmer, home monitor, or handheld appliance. Examples of communication techniques used by IMD 10 include low frequency or radiofrequency (RF) telemetry, which may be an RF link established via Bluetooth, WiFi, or MICS. IMD 10 may receive programming commands and algorithms from external device 150 via telemetry link 152 with telemetry module 106. For example, external device 150 may be used to program short circuit detection parameters used by controller 112. Telemetry module 106 may be controlled by controller 112 for delivering a patient or clinician alert or notification to external device 150 in response to detecting a short circuit condition.

IMD 10 may optionally be equipped with alarm circuitry 110 for notifying the patient or other responder that a patient alert condition has been detected by IMD 10. In one embodiment, the alarm 110 may emit an audible tone or notification to alert the patient or a responder that immediate medical attention is required. For example, when a short circuit condition is detected, particularly a short circuit involving HV coil electrodes 34 and 36 or their respective conductors, alarm 110 may be used to notify the patient, a caregiver or other responder that medical attention is required. In some embodiments, alarm 110 calls an emergency number directly via a wireless communication network.

Figure 3:
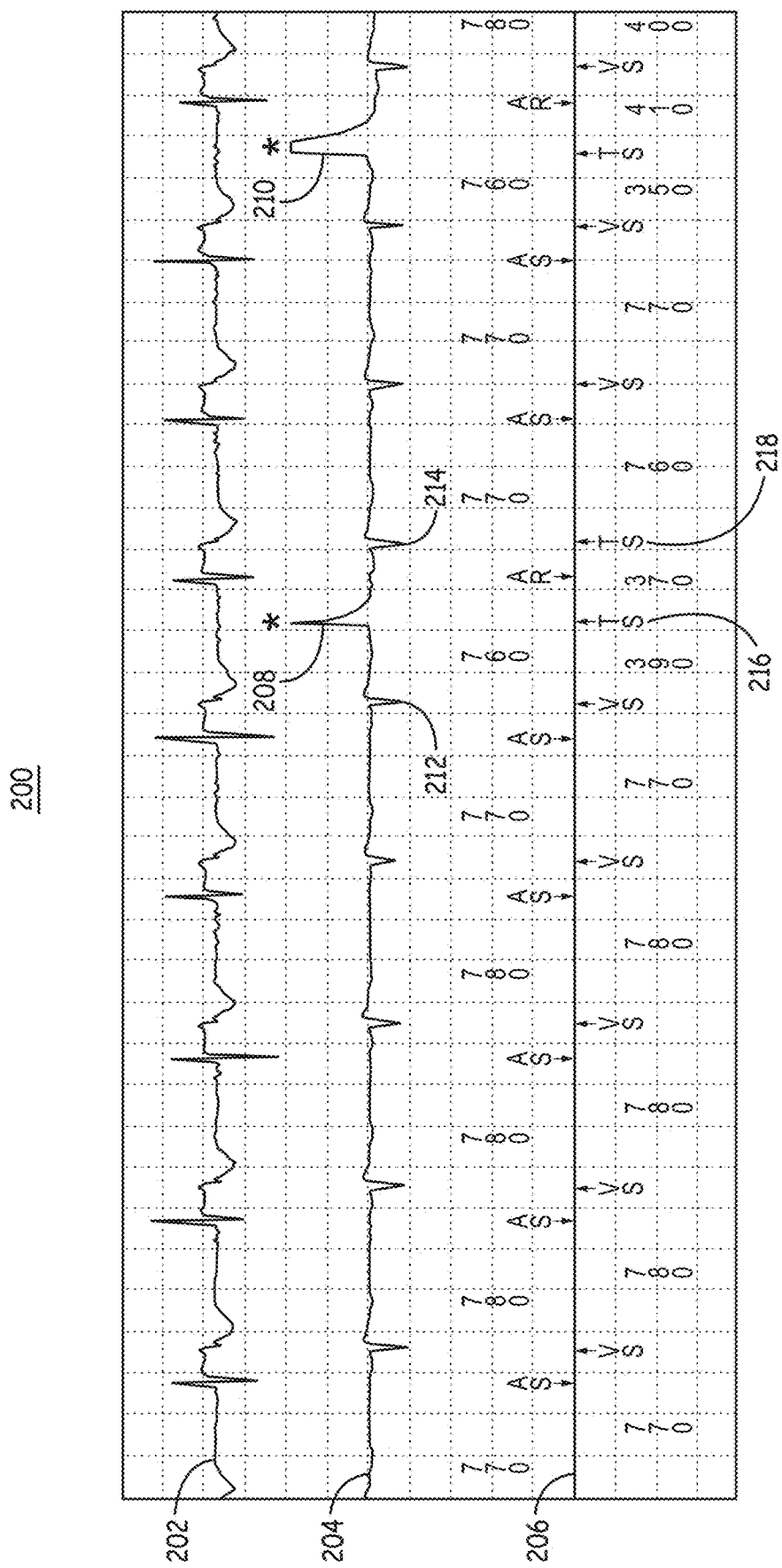
FIG. 3 shows cardiac electrogram (EGM) recordings that illustrate a signal corresponding to a short circuit condition.

FIG. 3 shows EGM recordings 200 that illustrate a signal corresponding to a short circuit condition. A NF EGM signal 202, recorded between a right atrial tip electrode and right atrial ring electrode is shown without short circuit noise signals. A FF EGM signal 204, recorded between an RV coil electrode and an SVC coil electrode, includes large noise signals 208 and 210 typifying signal events present during a potential short circuit condition associated with an insulation breach of the lead carrying the coil electrodes. These short circuit (SC) noise signals 208 and 210 are large in amplitude and leading edge slope, singular within the true RR interval, opposite in polarity than the true R-wave signals, and occur near a central portion of the RR interval, spaced out from the adjacent, immediately preceding R-wave 212 and subsequent R-wave 214.

The SC noise signal may be the only signal peak occurring between adjacent peaks corresponding to true R-waves when a short circuit condition is present. In rarer cases, more than one, typically not more than two, short circuit signal events occur during an RR interval, e.g. during a baseline interval of the EGM signal between two true R-waves. Accordingly, a short circuit signal event can be identified as an event crossing an SC detection threshold. The SC detection threshold is set to differentiate the SC signal event from true R-waves based on amplitude and/or polarity. The timing and number of SC signal events can be used to detect a potential short circuit condition and differentiate SC signal events from other types of noise. In one embodiment, an SC condition is detected in response to at least one EGM signal event having an amplitude crossing a short circuit detection threshold and being one of a maximum of two SC signal events occurring between two adjacent events having amplitudes not crossing the SC detection threshold. The two adjacent events may correspond to normal R-waves defining an RR interval. The maximum of two short circuit signal events occurring during the RR interval, e.g., along a baseline portion of the RR interval, typifies the type of noise signal present during a short circuit condition due to a lead insulation breach.

A marker channel 206 depicts sensed events and measured event intervals. The large SC noise signals 208 and 210 are sensed as tachycardia events (TS) 216, as indicated on the marker channel, when the noise signals 208 and 210 occur within a tachycardia detection interval after the preceding R-wave. The subsequent R-wave 214 may also be sensed as a tachycardia event 218 if sensed within a tachycardia detection interval after the SC noise signal 208, which has been falsely sensed as an R-wave. As such, SC noise signals 208 and 210 may lead to R-wave oversensing and false positive ventricular tachycardia (VT) or ventricular fibrillation (VF) detection. An unnecessary therapy may result, unnecessarily using IMD battery energy. If the therapy is delivered using one or both of the RV coil electrode and SVC coil electrode associated with the SC noise signals, the therapy energy may be shorted, prematurely draining battery energy. If a therapy is delivered in response to an appropriately detected VT or VF, the short circuit condition may prevent adequate cardioversion or defibrillation therapy from being delivered to the patient.

The characteristic SC noise signal 208, 210, however, may be used to monitor for a short circuit condition. The SC noise signal 208, 210 may be distinct from other types of noise, such as low amplitude muscle noise, electromagnetic interference (EMI) noise, or noise associated with a lead conductor fracture. Other types of noise may be present in sustained or short bursts of noise signals as compared to the single noise spike of the SC noise signal 208, 210. Other types of noise may be relatively low amplitude and may be randomly located in the EGM signal relative to true sensed R-waves as compared to the relatively high amplitude SC noise signals 208, 210 occurring during a mid-portion of the RR interval. Additionally, an SC noise signal sensed on the FF EGM signal sensed between the RV coil and SVC coil electrodes is typically opposite in polarity than true R-wave signals.

Multiple EGM signals may be monitored to identify an SC condition. As shown in FIG. 3, a NF EGM signal 202, which may be an atrial signal or a ventricular signal, may be monitored simultaneously with the FF EGM signal 204. True R-waves sensed on a FF EGM signal typically have relatively lower slope and/or lower amplitude than R-waves sensed on a NF ventricular EGM signal. The high amplitude, high slope SC noise signal may therefore be more readily distinguished from true R-waves on a FF EGM signal. In some embodiments, both a FF and NF EGM signal may be sensed to enable comparisons between sensed events. Noise signals 208 and 210 are strikingly dominant on the FF EGM signal 204 and substantially absent from the NF EGM signal 202. Accordingly, a signal 208, 210 meeting other SC detection criteria that is not sensed on a NF EGM signal 202 may be detected as an SC noise signal.

Figure 4:
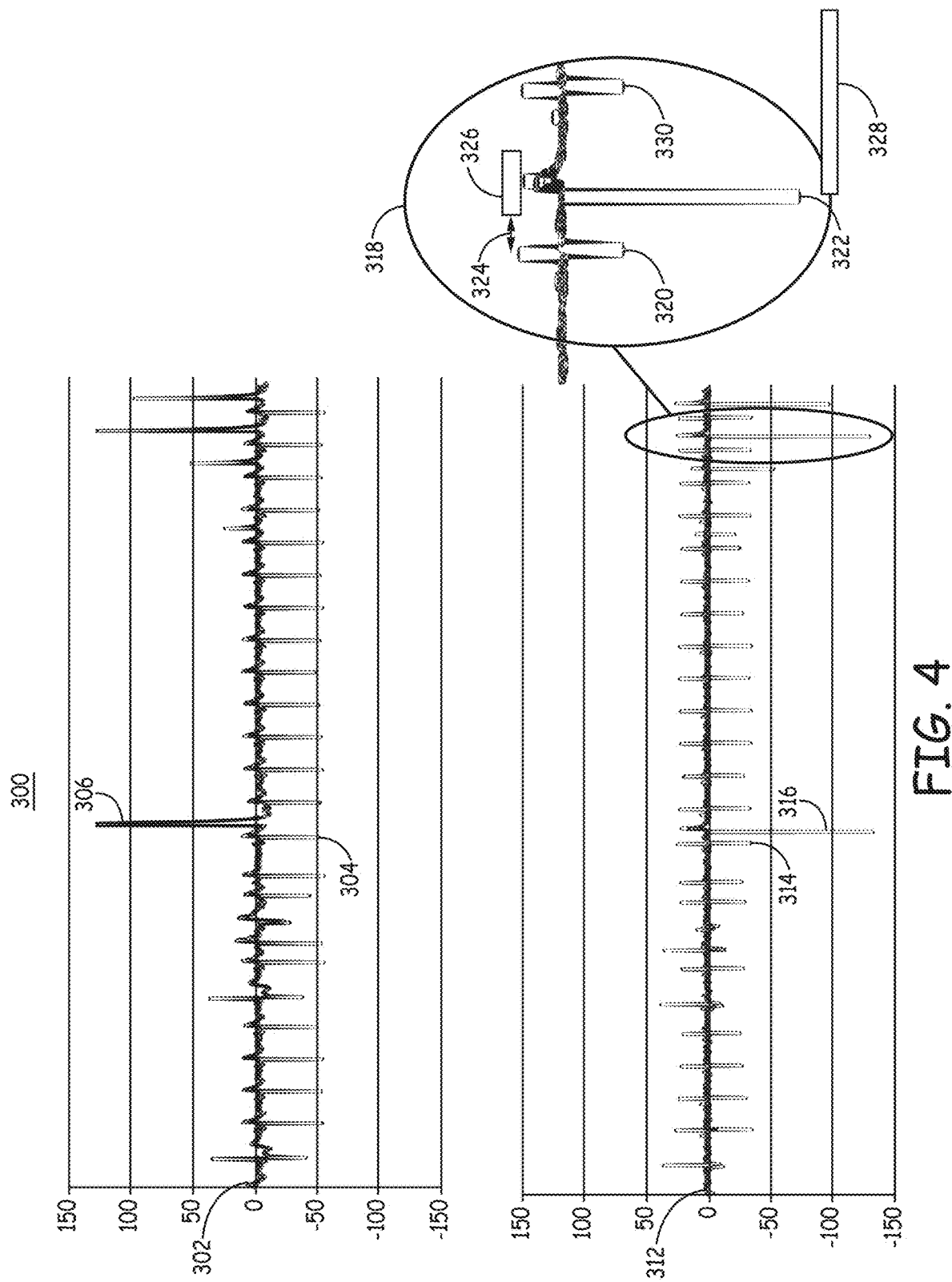
FIG. 4 shows recordings of a far-field EGM signal and a differential EGM signal illustrating one technique for detecting short circuit (SC) noise signals according to some embodiments.

FIG. 4 shows recordings 300 of a FF EGM signal 302 (RV coil to SVC coil) and a differential EGM signal 312 illustrating one technique for detecting SC noise signals according to some embodiments. A large SC noise signal 306 is observed during an RR interval, following an R-wave 304 that is relatively much smaller in amplitude (absolute value). The R-waves in EGM signal 302 are generally of consistent amplitude and polarity.

A differential EGM signal 312 is computed from the raw EGM signal 302. The SC noise signal 316 is still clearly observed and the difference in the amplitude of the SC noise signal 316 and the R-wave signal 314 is even more pronounced than in the raw EGM signal 302. The differential EGM signal 312 is a first order differential signal wherein the amplitude of each differential signal sample point is determined by computing the successive amplitude differences between raw EGM signal sample points, e.g. {n−(n−1)}. While a first order differential signal is shown here, it is contemplated that higher order differential signals could be used for differentiating and identifying SC noise signals from adjacent true R-wave signals.

In some embodiments, the amplitude of the raw EGM signal and/or the differential EGM signal 312 may be compared on a sample-by-sample basis to an SC detection threshold for detecting SC signals 306 and/or 316. In other embodiments, the peak amplitude following the timing of an R-wave sense signal may be compared to the SC detection threshold. Both the true R-waves and the SC signal 306 will be detected as R-waves. As such, the timing of an R-wave sense signal received from a sense amplifier in sensing module 102 may be used to start searching for a subsequent signal peak. If the peak amplitude of the sensed signal is greater than the SC detection threshold, the signal is detected as an SC event.

The SC detection threshold may be set in a variety of ways. Since the difference between an SC noise signal 306, 316 and a true R-wave is expected to be large, a nominal threshold, e.g. in the range of 50 to 100 A/D units in the example shown, may be set as an SC detection threshold. In other embodiments, a patient-specific threshold may be set based on sensed R-wave amplitudes. A peak amplitude may be compared to a preceding peak amplitude, e.g. the peak of SC noise signal 316 of the differential signal 312 may be compared to the peak amplitude of the immediately preceding peak 314 of the differential signal 312 to identify signal 316 as an SC noise signal. If the difference between successive peak amplitude values (which may be absolute values) is greater than a predetermined threshold, the larger peak is detected as an SC noise signal.

Alternatively, a measure of multiple preceding R-wave amplitudes, e.g. a running average or other distribution measurement of preceding R-waves, may be determined and used to set an SC detection threshold. For example, an SC detection threshold may be set as some percentage greater than one or more preceding R-wave amplitudes. In one illustrative example, the SC detection threshold is 20% greater than a running average of 12 R-wave peak amplitudes. In another embodiment a non-parametric method for setting an SC detection threshold may include determining a desired number of consecutive R-wave peak amplitudes and using the nth highest peak amplitude value. For example, the most recent 12 R-wave peak amplitudes may be determined and the $3^{rd}$ highest peak amplitude value may be used to set an SC detection threshold. When comparing peak amplitudes, absolute values may be used.

If the raw EGM signal 302 is being used to identify SC noise signals, an SC detection threshold may be set as some threshold opposite in polarity than a typical R-wave peak or a typical QRS signal amplitude range. For example, using the raw EGM signal, the minimum and maximum amplitude values over a specified time range (e.g. approximately 10 seconds) may be determined during normal sensing conditions (i.e. no noise signals). If the range is, for example, between a minimum of −50 A/D units and a maximum of 10 A/D units, an SC detection threshold could be defined as any signal crossing a positive polarity threshold, e.g. +25 A/D units. In other words, an SC detection threshold may be established that allows detection of an abrupt polarity change outside a "normal" amplitude and polarity range of the raw EGM signal.

In addition to an amplitude- and/or polarity-based SC detection threshold, a timing-based SC detection threshold may be established. An SC detection window may be set at a predetermined interval after a sensed R-wave. For example, as shown in the enlarged view 318 of a portion of differential signal 312, an SC detection window 326 may be set to begin a predetermined interval 324 after a sensed R-wave 320. For example, SC detection window 326 may begin at approximately 100 to 300 ms following an R-wave sense signal 320 and may be approximately 100 to 300 ms in duration. If a single signal 322, or a maximum of two signals, exceeding the SC detection amplitude threshold (using either the raw and/or differential signal) is sensed or identified during the SC detection window 326, the signal 322 may be detected as an SC signal. The SC detection window 326 may be set following signal events that do not cross the SC detection threshold, i.e. signal events corresponding to true R-waves.

An additional criterion may be applied that requires that only a single sensed event occurs during a subsequent monitoring window. For example, a normally sensed R-wave 330 or no signal at all may be sensed within a predetermined next time window 328 following the suspected SC noise signal 322. The next time window 328 may be set approximately equal to an expected RR interval, a window that is at least half of an RR interval since SC noise signal 322 is expected to occur in a mid-portion of the RR interval, or may be equal to SC noise detection window 326 started in response to the false sensing of the SC noise signal 322 as an R-wave. Such timing-based criteria for detecting an SC signal associated with an insulation breach may be used to positively identify the characteristic high amplitude, single noise spike that may typically occur in a mid-portion of the true RR interval, or in some cases a maximum of two SC signal events between two adjacent true R-waves.

Figure 5:
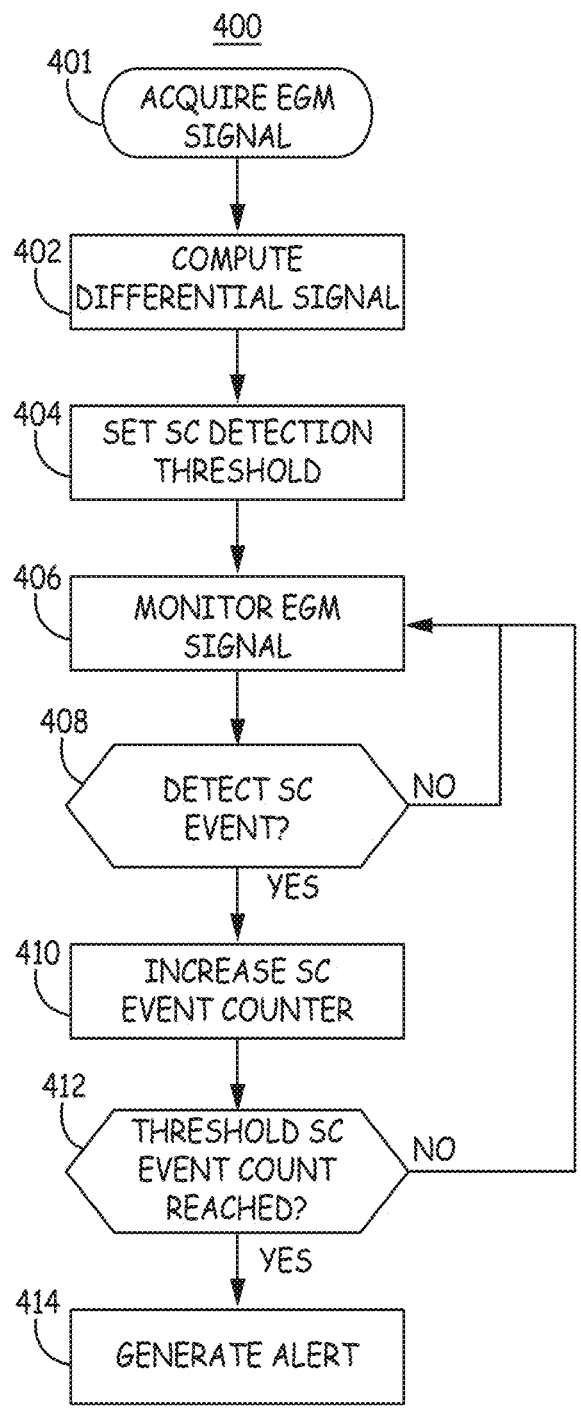
FIG. 5 is a flow chart of a method for monitoring for a short circuit condition according to one embodiment.

FIG. 5 is a flow chart 400 of a method for monitoring for a short circuit condition according to one embodiment. Flow chart 200 is intended to illustrate the functional operation of the IMD 10, and should not be construed as reflective of a specific form of software or hardware necessary to practice the methods described. It is believed that the particular form of software will be determined primarily by the particular system architecture employed in the IMD and by the particular detection and therapy delivery methodologies employed by the device. Providing software, hardware and/or firmware to accomplish the described functionality in the context of any modern IMD, given the disclosure herein, is within the abilities of one of skill in the art. Methods described in conjunction with flow charts presented herein may be implemented, at least in part, in a non-transitory computer-readable medium that stores instructions for causing a programmable processor to carry out the methods described. The instructions may be implemented as one or more software modules, which may be executed by themselves or in combination with other software by controller 112 in cooperation with therapy delivery module 104 and sensing module 102.

At block 401, an EGM signal is sensed. In one embodiment, the EGM signal is a FF EGM. The FF EGM signal being monitored for an SC condition will typically include at least one HV coil electrode and may be between two HV coil electrodes, such as RV coil 34 and SVC coil 36 shown in FIG. 1. With reference to IMD 10 shown in FIG. 2, sensing module 102 provides a digitized FF EGM signal to controller 112 for monitoring for SC signals.

At block 402, the controller 112 computes a differential signal of the raw digitized EGM signal. It is contemplated that in some embodiments, SC detection criteria may be applied to the raw digitized EGM signal additionally or alternatively to the differential EGM signal. As described above, however, the differential signal is expected to provide a greater difference between true R-wave signal amplitude and slope and SC noise signal amplitude and slope, which may increase the reliability of SC noise signal detection.

An SC detection threshold is established at block 404. The SC detection threshold may include any combination of an amplitude-based threshold (including polarity change detection) and the timing-based thresholds as described above. For example, a nominal amplitude threshold and SC detection window may be applied by controller 112 for detecting SC noise signals. Alternatively, a patient-specific amplitude threshold may be computed by controller 112 using previously sensed R-waves. A patient-specific SC detection window may be computed based on previously measured RR intervals. Patient-specific amplitude thresholds and SC detection windows may be updated over time using running averages, an nth largest value out of m values, or other updated measurements of R-wave amplitude and RR intervals.

At block 406, the controller 112 monitors the FF EGM signal events for SC noise signals, also referred to herein as "SC events," by applying the SC detection threshold criteria to the differential signal. If an SC noise signal is detected at decision block 408, an SC event counter may be increased at block 410. The raw and/or differential EGM signals that resulted in increasing the SC event counter may be stored in IMD memory 108, for example along with marker channel data, for later retrieval and review by a clinician or other expert for confirmation of a short circuit condition. If the SC event counter reaches a threshold event count, as determined at block 412, an alert signal is generated at block 414. A patient alert may be generated by the IMD 10 and/or a telemetry alert signal may be transmitted to an external device 150 via wireless telemetry to notify the patient or a clinician of the detected SC condition. In some embodiments, a single detected SC noise signal may trigger an alert at block 414. In other embodiments, a threshold number, e.g. three or more SC events, may be required before triggering an alert.

Figure 6:
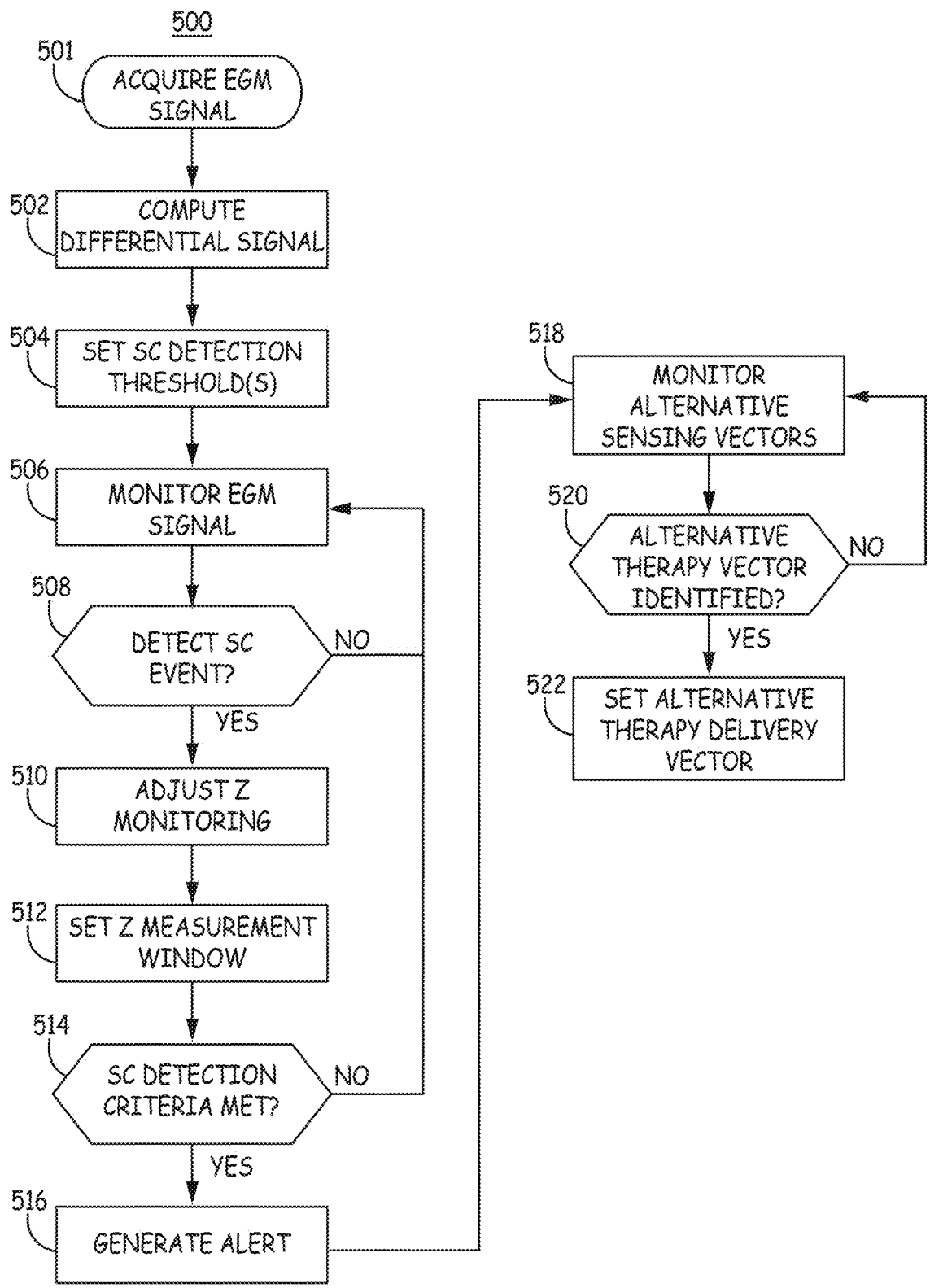
FIG. 6 is a flow chart of a method for detecting and responding to an SC condition according to an alternative embodiment.

FIG. 6 is a flow chart 500 of a method for detecting and responding to an SC condition according to an alternative embodiment. At block 501, an EGM signal, typically a FF EGM signal including RV coil electrode 34 and SVC coil electrode 36 is acquired. At block 502, a differential signal of the raw EGM signal is computed by controller 112. The controller 112 establishes SC detection thresholds at block 504, e.g. according to programmed nominal values and/or measured R-wave amplitude, R-wave polarity, RR intervals or any combination thereof, for detecting SC noise signals.

The controller 112 monitors the EGM signal for SC noise by applying the SC detection threshold criteria to the differential signal at block 506 as described previously herein.

If at least one SC signal event is detected at block 508, controller 112 adjusts the impedance (Z) monitoring performed by sensing module 102 to increase the likelihood of measuring an impedance change associated with the short circuit condition. Impedance monitoring may typically be performed once per day or perhaps every six hours or some other periodic interval. In response to detecting one or more SC signals at block 508, controller 112 adjusts impedance monitoring performed by sensing module 102 to include frequent impedance measurements of the FF EGM sensing vector pathway, or whichever EGM sensing pathway was used to detect the SC signal event(s). For example, the impedance may be measured hourly, every 30 minutes, every 15 minutes, or some other periodic interval that is relatively more frequent than the previous impedance monitoring schedule being used by sensing module 102. The increased frequency of impedance monitoring may be performed at frequent intervals, e.g. every 30 minutes, for some interval of time, e.g. 12 or 24 hours, after detecting an SC noise signal.

In addition to adjusting a frequency of impedance monitoring, an impedance monitoring window may be set at block 512 in an attempt to measure the impedance of the sensing pathway during or near the expected time of an SC noise signal, i.e., approximately a mid-portion or baseline portion of the RR interval. Accordingly, an impedance measurement window may be set at block 512 that corresponds approximately to an SC detection window as described above in conjunction with FIG. 4. The impedance may be measured continuously during the impedance measurement window or repeatedly during the impedance measurement window, e.g. two or more times during the measurement window. It is recognized that impedance monitoring may occur both within and outside an impedance measurement window set to specifically identify a change in impedance that may occur during a mid-portion or baseline portion of the RR interval associated with an SC signal.

At block 514, the controller 112 determines if the SC detection criteria are met. SC detection criteria may include a predetermined number of SC signal events being detected and may include detection of a change in impedance of the sensing pathway. A change in impedance may be a decrease in impedance, occurring within or outside an impedance measurement window, as compared to one or more previous impedance measurements.

In response to detecting an SC condition, an alert is generated at block 516. In addition to generating an alert, alternative sensing vectors may be monitored at block 518 for detecting the SC condition. One or more alternative EGM sensing vectors may be monitored by controller 112 to detect SC noise signals. For example, if SC noise signals are detected on the FF EGM signal sensed between the RV coil and SVC coil electrodes, an EGM signal sensed between the RV coil and the RV tip or RV ring electrode and an EGM signal sensed between the SVC soil and the RV tip or RV ring electrode may both be monitored to determine if a different sensing pathway does not result in SC noise signal detection. Other available LV sense/pace electrodes may be paired with the RV coil and with the SVC coil until a pathway is identified that does not result in SC noise signal detection. It is recognized that for different sensing pathways, different SC detection thresholds may be used.

If an alternative sensing pathway can be identified at block 520 that does not include SC noise signals, a therapy delivery vector may be set by the controller 112 at block 522 using this information. For example, if an SVC coil to RV tip sensing pathway results in no SC noise signal detection but the RV coil to RV tip sensing pathway does result in SC noise signal detection, a HV therapy delivery vector may be selected to include the SVC coil and exclude the RV coil for delivering HV cardioversion or defibrillation shocks. In this way, controller 112 can use SC condition detection results to identify a therapy delivery pathway and control therapy delivery module 104 to deliver therapy, at least a high voltage therapy, as needed using a pathway that may exclude the short circuit condition.

Figure 7:
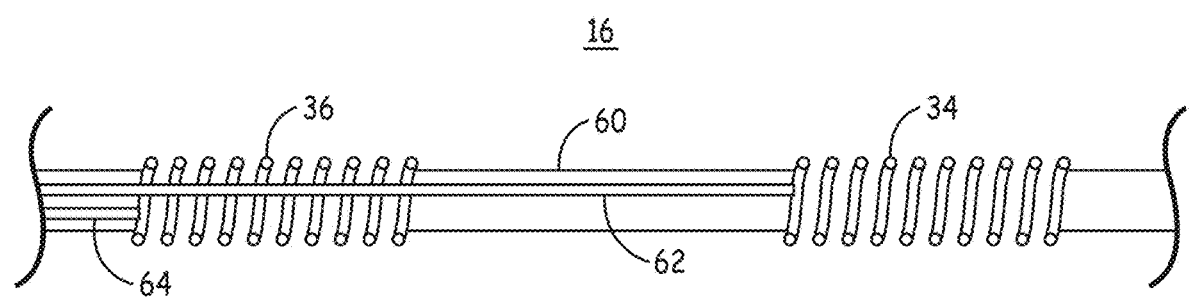
FIG. 7 is a conceptual diagram of the right ventricular lead shown in FIG. 1.

FIG. 7 is a conceptual diagram of RV lead 16 shown in FIG. 1. RV coil electrode 34 and SVC coil electrode 36 are shown extending along the outside of electrically insulating lead body 60. An RV coil conductor 62 is an insulated conductor extending from RV coil electrode 34 to the proximal lead connector (not shown). An SVC coil conductor 64 is an insulated conductor extending from SVC coil electrode 36 to the proximal lead connector. The RV coil conductor 62 extends within lead body 60 passing through SVC coil electrode 36. If the electrical insulation between RV coil conductor 62 and SVC coil electrode 36 is breached, a short circuit condition may occur between SVC coil electrode 36 and conductor 62. In another example, a breach of the electrical insulation between RV coil conductor 62 and SVC coil conductor 64 may result in a short circuit condition. An electrical short between these high voltage electrode components of lead 16 may not be detected during standard low voltage impedance monitoring and may be intermittent due to lead motion or shifting. The SC noise signals 208, 210 shown in FIG. 3 may be characteristic of the type of short circuit condition that may occur between RV coil conductor 62 and SVC coil electrode 36 or between the RV coil conductor 62 and SVC coil conductor 64.

Figure 8:
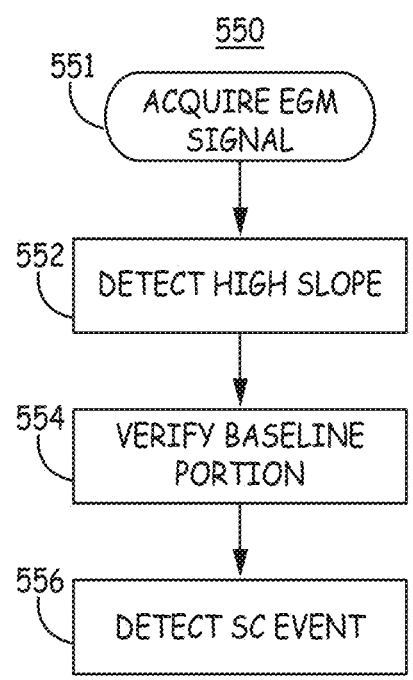
FIG. 8 is a flow chart of a method for detecting an SC event according to another example.

FIG. 8 is a flow chart 550 of a method for detecting an SC event according to another example. At block 551, an EGM signal is acquired by the sensing module 102. In one example, a FF EGM is acquired at block 551 between the RV coil electrode 34 and the SVC coil electrode 36 (both shown in FIG. 1) for detecting the type of short circuit condition described in conjunction with FIG. 7. The RV and SVC coil electrodes are carried by the same lead and each have insulated conductors extending from the proximal lead connector to the respective electrodes. More generally, the EGM signal acquired at block 551 is acquired between any two electrodes carried by a single lead and each coupled to an insulated conductor extending next to each other within the lead body or next to the other electrode positioned along the lead body. An insulation breach of one of the insulated conductors could cause a short circuit between the conductor and the other electrode, such as the insulation breach described above between the RV coil electrode conductor and the SVC coil electrode. If a breach occurs in the insulation of both the conductors, a short circuit may occur between the two conductors, such as between the RV coil conductor and the SVC coil conductor as described above. The methods disclosed herein are useful in detecting this type of short circuit condition between an electrode and a conductor or between two conductors of a medical electrical lead.

The EGM signal is monitored at block 552 to detect a high slope of the signal. A high slope may be based on a first order or higher differential signal crossing a threshold as described above. In one example, the controller 112 detects a high slope at block 552 based on a single sample point difference determined as the amplitude difference between a pair of consecutive EGM signal sample points. If the single sample point difference exceeds an SC threshold, a high slope is detected that may be an SC event. In other embodiments, a sum of successive sample point differences may be compared to an SC threshold. For example, the sum of the amplitude differences between at least two consecutive pairs of consecutive sample points may be compared to an SC threshold (i.e. sum=$(n_{+1}-n)+(n_{+2}-n_{+1})$ ...).

At block 554, the controller 112 verifies that the high slope detected at block 552 is being detected during a baseline portion of the EGM signal. The "baseline portion" of a cardiac electrical signal as used herein refers to a portion of the signal that occurs outside the QRS segment that is associated with the myocardial depolarization phase of the ventricles. The baseline portion occurs between R-waves attendant to the ventricular depolarization phase. The baseline portion may include a P-wave (attendant to the atrial depolarization phase) that precedes the QRS segment and the T-wave (attendant to the ventricular repolarization phase) that follows the QRS segment. The P-wave is typically a low amplitude signal that may not be discernable on the FF EGM signal in some cases. The T-wave may be observable, but is generally a low amplitude and low slope signal compared to the R-wave and a much lower slope and amplitude than an SC noise signal. Motion of the lead due to atrial contraction may cause intermittent SC noise signals to appear on the EGM signal due to a short circuit between a lead conductor and a nearby electrode normally insulated from the lead conductor or between two lead conductors.

A baseline portion is verified to at least precede the detected high slope to verify that the high slope is along a leading edge of the detected signal. The high slope leading edge of the SC noise signals 208, 210 occurring during the baseline portion allow the SC noise signals 208, 210 to be distinguished from relatively lower leading edge R-wave signals 212, 214. A baseline portion of the EGM signal may optionally be verified to occur after detecting the high slope in addition to preceding the detected high slope. In response to detecting a signal slope exceeding an SC threshold and verifying that the slope is detected during a baseline portion of the EGM signal, an SC event is detected at block 556. An SC condition may be detected and responded to (e.g., by generating an alert and/or selecting a therapy vector that avoids the SC condition) upon a single SC event detection or upon detecting a required minimum number of SC events. Accordingly, the method for detecting an SC event shown in FIG. 8 and other flow charts presented herein may be implemented in conjunction with the responses to an SC condition disclosed herein including generating an alert, selecting a therapy vector that avoids the short circuit condition or otherwise adjusting a therapy delivery, and/or adjusting an impedance monitoring protocol.

The method described in conjunction with FIG. 8 and other methods disclosed herein refer to an EGM signal that is acquired from a transvenous lead carrying intracardiac electrodes and monitored for detecting SC events. It is contemplated, however, that the methods disclosed herein for detecting an SC condition may be used to detect an SC condition in an extracardiac or non-transvenous lead, such as in a subcutaneous, substernal, pericardial, epicardial or other extracardiac or non-transvenous lead. An ECG signal may be acquired at block 551 using an extracardiac or extravascular implantable medical electrical lead that carries multiple electrodes. An SC condition between an electrode and a conductor or between two conductors may be detected by sensing an ECG signal between electrodes carried by a non-transvenous lead (for example implanted subcutaneously or within the thorax but outside the heart) using the techniques disclosed herein.

Figure 9:
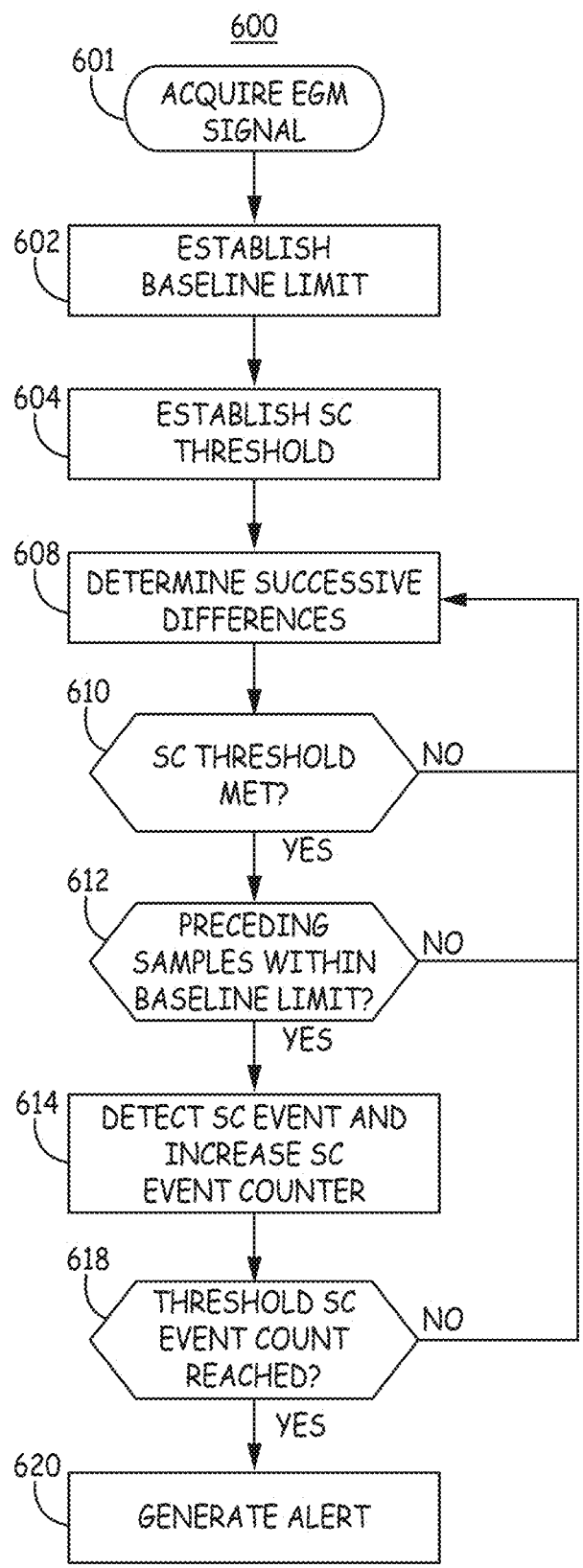
FIG. 9 is a flow chart of a method for detecting and responding to an SC condition according to another example.

FIG. 9 is a flow chart 600 of a method for detecting and responding to an SC condition according to another example. At block 601, an FF EGM signal is acquired by the sensing module 102, for example between the RV coil electrode and SVC coil electrode. At block 602, a baseline limit is established and stored in ICD memory 108 for use by the controller in recognizing signal samples that fall within a baseline variation of the FF EGM signal. The baseline limit may be established as a nominal value. For example, the baseline limit may be established as an amplitude change of less than 0.1 mV (or other value) between consecutive signal sample points.

The baseline limit may alternatively be established by determining signal sample amplitudes during a baseline portion of the acquired FF EGM signal between consecutively sensed R-waves. For example, an RR interval may be measured between consecutively sensed R-waves, and a baseline window may be set during a mid-portion of the RR interval. A baseline portion from which signal sample point amplitudes and differences are determined for establishing a baseline limit may be determined automatically by the IMD 10, determined automatically by the IMD 10 and confirmed by the user, or selected manually by a user interacting with a programmer (e.g., external device 150 shown in FIG. 2).

The established baseline limit may require a minimum number of signal sample points within an established amplitude limit and/or sample point difference limit to confirm a baseline portion of the EGM signal. In one example, at least five consecutive signal sample points (or other selected number of points) must have less than a 0.1 mV amplitude difference between each consecutive pair of the signal sample points in order to verify that the five sample points are a baseline portion of the EGM signal. Alternatively, a baseline limit may be established as a maximum sum of successive differences between each consecutive pair of a predetermined number of consecutive sample points. The baseline limit may require a predefined number of sample points out of a larger number of consecutive sample points (i.e. X out of Y sample points, for example 5 out of 7 sample points) that satisfy the amplitude or difference limit. The amplitude or difference limit may be selected to be high enough to account for the possibility of the SC event occurring during a P-wave or a T-wave during the baseline portion of the EGM signal.

At block 604, an SC threshold is established for detecting a high slope of the EGM signal characteristic of an SC noise signal. The SC threshold may be established as a difference threshold between consecutive EGM signal sample points. A large difference between two consecutive sample points is indicative of the relatively high slope of the leading edge of the SC noise signals 208, 210 shown in FIG. 3. This very steep slope along the leading edge of the noise signals 208, 210 is characteristically higher than the trailing edge of the noise signals 208, 210 as seen in FIG. 3. The high slope leading edge followed by a lower slope trailing edge differentiates the SC noise signals 208, 210 from the R-waves 212, 214 which have relatively lower leading edge slopes and may have less of a difference between their leading and trailing edge slopes.

In one example, an SC threshold for detecting a high slope of an SC noise signal is an amplitude difference between two consecutive sample points of at least 5 mV. The SC threshold set at block 604 may be set to a nominal value or based on a slope determined from R-waves 212, 214 (FIG. 3). For example, the SC threshold may be set to the slope of an R-wave plus a fixed value or percentage greater than the R-wave slope. The SC threshold may be determined automatically by the IMD 10, determined automatically by the IMD 10 and confirmed by the user, or selected manually by a user interacting with a programmer (e.g., external device 150 shown in FIG. 2).

At block 608, the FF EGM signal is monitored for an SC condition by determining differences between consecutive signal sample points. Successive sample point differences may be determined and stored in a memory buffer for a predetermined number of sample points as required for detecting the SC event. The number of sample points required to detect an SC event includes a first number of points required to determine if the SC threshold is met for detecting a high slope and a second number of points required to verify that the SC threshold is met during a baseline portion of the EGM. An abrupt change in the difference between consecutive sample points indicative of a high slope leading edge of an event signal immediately preceded by sample points confirmed to be within an EGM baseline portion is evidence for the detection of the SC event. Therefore, successive sample point amplitude differences (or signal sample point amplitudes) are stored as needed for comparing to the baseline limit criteria if one or more sample point differences meet the SC threshold.

If a consecutive sample point amplitude change is greater than the SC threshold, as determined at block 610, preceding sample points are analyzed at block 612 to determine if they are within the established baseline limit. In one illustrative example, if the amplitude difference between two consecutive sample points is greater than 5 mV, then the successive differences between the preceding five consecutive sample points is compared to the established baseline limit, e.g. 0.1 mV. If the five previous successive differences are all less than 0.1 mV, the baseline limit is met at block 612.

It is recognized that in some cases one or more sample points may occur between the sample points satisfying the SC threshold requirement and the sample points satisfying the baseline limit requirement. For example, the EGM signal may begin to increase from baseline but not reach the SC threshold difference for two or more sample points after the baseline portion. Accordingly, criteria for detecting the SC event may include verifying the baseline portion within a predefined time interval or number of sample points preceding the sample points satisfying the SC threshold requirement.

If either of the SC threshold or the baseline limit is not met, the controller continues to monitor the FF EGM for an SC event by returning to block 608. If both the SC threshold and baseline limit criteria are met at decision blocks 610 and 612, an SC event is detected at block 614 based on a high slope evidenced by a large sample point amplitude difference preceded by a confirmed baseline portion of the EGM signal evidenced by low sample point amplitude difference. An SC event counter may be increased at block 614 such that an SC alert is generated at block 620 after a threshold SC event count is reached at block 618. Alternatively, an SC alert may be generated at block 620 based upon a single SC event being detected at block 614. As described previously, the IMD 10 may alter a therapy vector to exclude the short circuit and/or adjust an impedance monitoring protocol to gather additional evidence of the SC condition in response to detecting the SC event.

Figure 10:
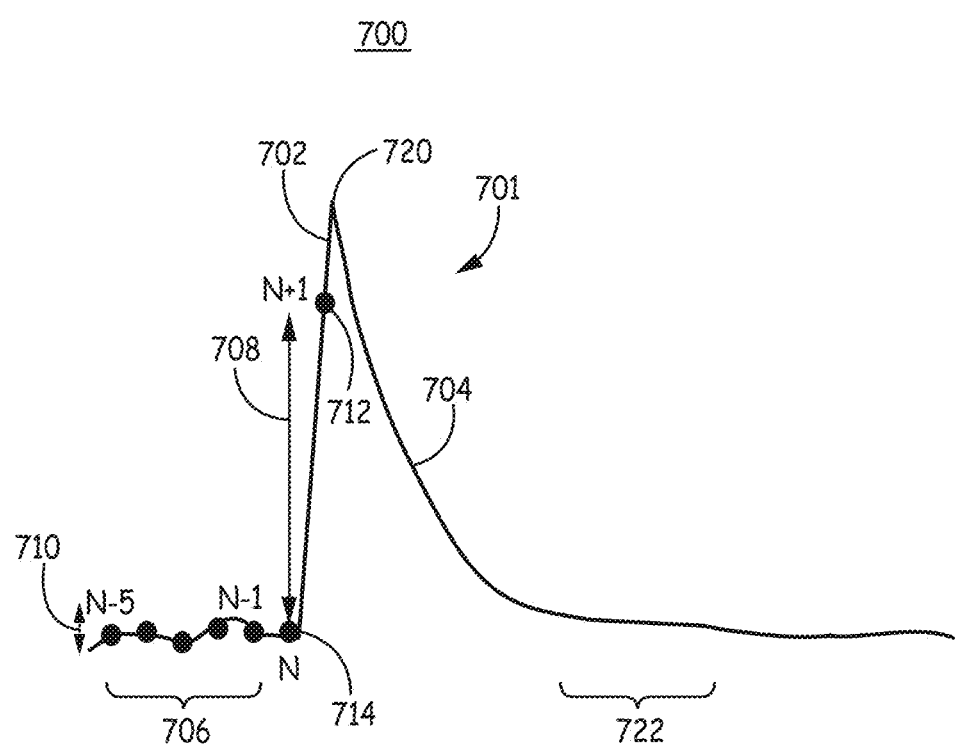
FIG. 10 is a conceptual diagram of the SC event detection process described in conjunction with the flow chart of FIG. 9.

FIG. 10 is a conceptual diagram of an EGM signal 700 including an SC noise signal 701 that is detected as an SC event according to the detection process described in conjunction with FIG. 9 and/or variations of that process as described below. The SC noise signal 701 is shown following a baseline portion 706 of the EGM signal 700 and has a high slope leading edge 702 and a relatively lower slope trailing edge 704. The high slope leading edge 702 is detected based on a sample point difference 708 between consecutive signal sample points N 714 and $N_{+1}$ 712 that exceeds an established SC threshold. When this requirement of the SC threshold is met, the controller analyzes preceding signal samples, e.g. sample point $N_{-1}$ through $N_{-5}$ (or another number of preceding sample points) to determine if sample points preceding the high slope condition of point N and $N_{+1}$ are baseline sample points.

The difference between each consecutive pair of sample points (i.e. $N_{-1}$-$N_{-2}$, $N_{-2}$-$N_{-3}$, $N_{-3}$-$N_{-4}$, etc.) may be compared to a baseline amplitude difference limit 710. If all four of the consecutive sample point differences between points $N_{-1}$ and $N_{-5}$ are within the baseline amplitude difference limit 710, the points $N_{-1}$ through $N_{-5}$ are verified as a baseline portion of the EGM signal 700 according to the established baseline limit of this illustrative example. In FIG. 10, the baseline portion sample points 706 immediately precede the sample points N and $N_{+1}$ satisfying the SC threshold. As indicated above, the sample points satisfying the baseline criteria may be separated by one or more intervening sample points from the sample points satisfying the SC threshold. The baseline portion may therefore be verified if X out of Y preceding sample points fall within the baseline limit criteria or if a baseline portion can be verified within a predefined number of sample points or time interval earlier than the points 712 and 714 meeting the SC threshold requirement.

It is recognized that numerous algorithms may be conceived for confirming that a predetermined number of sample points preceding the sample points which satisfy the SC threshold are baseline points. For example, the successive differences between the sample point amplitudes may be summed and compared to a baseline limit. In some examples, the controller verifies that a baseline portion 706 extends for a predetermined minimum number of sample points (or a minimum period of time) preceding the leading edge 702 (detected as the sample points satisfying the SC threshold). In one example, the controller verifies that at least the sample point N−1 immediately preceding the sample point N 714 and N+1 712 is within a baseline portion 706. Verification of the preceding baseline portion 706 verifies that the sample points N and $N_{+1}$ that satisfy the SC threshold are along the leading edge 702 of the signal peak 720, a distinguishing characteristic of the SC noise signals.

Once both criteria relating to detecting a high leading edge slope 702 during a verified baseline portion 706 are satisfied, signal 701 is detected as an SC event.

These criteria may be applied in conjunction with an SC event search window as described previously that is started at or a spaced apart time after sensing a valid R-wave. R-waves used to set an SC event search window may be sensed from the same EGM signal 700 or a different FF or NF EGM signal sensed using different electrodes (on the same lead or a different lead). The sensing module of the IMD is configured to generate cardiac sense event signals in response to sensing R-wave signals from an EGM signal. The IMD controller 112 may be configured to set an SC detection window having an onset spaced in time after an R-wave sense event signal received from the sensing module and detect SC events only during the SC detection window.

In some examples, additional criteria may be applied for detecting noise signal 701 as a short circuit event. For example, the slope of trailing edge 704 may be required to be less than the slope of leading edge 702. The relatively lower slope of trailing edge 704 may be detected, for example and without limitation, by searching for the signal peak 720, determining sample point amplitude differences occurring after peak 720 and comparing the sample point amplitude difference(s) to sample point amplitude differences prior to peak 720, along leading edge 702.

For example, the trailing edge sample point amplitude differences may be compared to difference 708 to verify that the slope is lower than the lead edge slope. The trailing edge sample point amplitude differences may alternatively be compared to two or more successive differences between two or more pairs of consecutive sample points after baseline portion 706 and before peak 720 or to the SC threshold used to detect high slope leading edge 702 to verify a lower slope along trailing edge 704 than the slope along leading edge 702. Alternatively, a sum of successive differences of sample point amplitudes occurring after peak 720 may be compared to a threshold or a sum of consecutive sample point amplitude differences occurring prior to peak 720. In this way, a relatively lower slope trailing edge 704 can be confirmed to follow the high slope leading edge 702 that occurs during the baseline portion 706 of the EGM signal 700.

Confirmation of a high slope leading edge and lower slope trailing edge may be based on determining a difference or ratio of the leading slope 702 and the trailing slope 704 and comparing that difference or ratio to an SC threshold. In some examples, the trailing edge slope of an SC noise signal is approximately 25% of the leading edge slope. In contrast, the R-wave trailing edge slope may be similar to or even greater than the R-wave leading edge slope. SC event detection criteria may require that the trailing edge slope 704 is less than the leading edge slope or less than a predetermined percentage, e.g., 50%, of the leading edge slope 702. Alternatively, if the trailing edge slope is at least or greater than the leading edge slope, or a percentage of the leading edge slope, the signal is not detected as an SC event and may be an R-wave. In this way, the SC noise signal 701 can be distinguished from an R-wave based on a relatively greater difference between the leading and trailing edge slopes of the SC noise signal 701 than the difference between leading and trailing edge slopes of an R-wave.

In addition to or alternatively to verifying a trailing edge 704 having a relatively lower slope than leading edge 702, the controller may verify a second baseline portion 722 following the high slope leading edge 702 (or lower slope trailing edge 704). Accordingly, in some examples, verifying that the high slope leading edge 702 occurs during a baseline portion of the FF EGM signal includes verifying a baseline portion 706 preceding leading edge 702 and verifying a baseline portion 722 subsequent to leading edge 702.

Baseline portion 722 may be verified using the same or similar criteria used to verify baseline portion 706. For example, amplitude differences between one or more consecutive sample point pairs may be required to be less than a baseline threshold or a sum of successive differences between consecutive sample points may be compared to a baseline threshold. Verifying that the high slope leading edge 702 occurs during a baseline portion of the EGM signal 700 may include verifying a return to a baseline portion 722 within a predetermined time interval or number of sample points after the SC threshold is met. In this way, a characteristic high slope leading edge signal occurring during a verified baseline portion of the EGM signal can be detected as an SC event.

Thus, a medical device and associated methods for detecting SC events and responding to an SC condition have been presented in the foregoing description with reference to specific embodiments. Various combinations or modifications of the illustrative embodiments may be conceived by one having ordinary skill in the art based on the teachings provided herein. For example, the techniques disclosed herein may be performed in a different order or combination than shown and described in conjunction with the drawings. It is appreciated that various modifications to the referenced embodiments may be made without departing from the scope of the disclosure and the following claims.

The invention claimed is:

1. A method comprising:
sensing a cardiac signal via a plurality of electrodes carried by an implantable medical electrical lead;
determining a slope of the cardiac signal with a controller;
comparing the slope of the cardiac signal to a short circuit threshold with the controller; and
detecting a short circuit event within the implantable medical electrical lead when the slope of the cardiac signal exceeds a short circuit threshold with the controller.

2. The method of claim 1, wherein determining the slope of the cardiac signal comprises determining a difference between a pair of sample points of the cardiac signal.

3. The method of claim 1, wherein determining the slope of the cardiac signal comprises determining a sum of successive differences between sample points.

4. The method of claim 1, further comprising:
verifying that the slope of the cardiac signal exceeded the short circuit threshold during a baseline portion of the cardiac signal, the baseline portion occurring between consecutive R-waves representative of ventricular depolarizations;
detecting the short circuit event upon verifying that the slope of the cardiac signal exceeded the short circuit threshold during the baseline portion of the cardiac signal; and
not detecting the short circuit event upon not verifying that the slope of the cardiac signal exceeded the short circuit threshold during the baseline portion of the cardiac signal.

5. The method of claim 4, wherein verifying that the slope of the cardiac signal exceeded the short circuit threshold during the baseline portion of the cardiac signal further comprises:
determining a difference between at least one pair of sample points that precede samples used to determine the slope of the cardiac signal; and
verifying that the slope of the cardiac signal exceeded the short circuit threshold during the baseline portion of the cardiac signal in response to the difference being less than a baseline threshold.

6. The method of claim 4, wherein verifying that the slope of the cardiac signal exceeded the short circuit threshold during a baseline portion of the cardiac signal further comprises:
determining a sum of differences between a plurality of pairs of sample points that precede samples used to determine the slope of the cardiac signal;
comparing the sum to a baseline threshold; and
verifying that the slope of the cardiac signal exceeded the short circuit threshold during the baseline portion of the cardiac signal in response to the sum being less than the baseline threshold.

7. The method of claim 4, wherein verifying that the slope of the cardiac signal exceeded the short circuit threshold during the baseline portion of the cardiac signal further comprises verifying a first baseline portion preceding the slope and a second baseline portion occurring after the slope.

8. The method of claim 1, further comprising:
generating a cardiac sense event signal in response to sensing an R-wave from the cardiac signal;
setting a short circuit detection window having an onset spaced in time after the cardiac sense event signal is received; and
detecting the short circuit event only during the short circuit detection window.

9. The method of claim 1, further comprising verifying the slope is a leading edge of a signal peak occurring during a baseline portion of the cardiac signal, the baseline portion occurring between consecutive R-waves representative of ventricular depolarizations.

10. The method of claim 1, further comprising:
determining a trailing edge slope of the cardiac signal occurring during a baseline portion of the cardiac signal, the baseline portion occurring between consecutive R-waves representative of ventricular depolarizations;
comparing the trailing edge slope to the slope that exceeds the short circuit threshold; and
detecting the short circuit event in response to the trailing edge slope being less than the slope that exceeds the short circuit threshold and the trailing edge slope occurring after the slope that exceeds the short circuit threshold.

11. The method of claim 1, further comprising performing an action in response to detecting the short circuit, wherein the action comprises one of generating an alert signal and adjusting a therapy delivery pathway.

12. An implantable medical device comprising:
sensing circuitry configured to sense a cardiac signal; and
a controller electrically coupled to the sensing circuitry and configured to receive the cardiac signal, determine a slope of the cardiac signal, compare the slope of the cardiac signal to a short circuit threshold, and detect a short circuit event when the slope of the cardiac signal exceeds the short circuit threshold.

13. The device of claim 12, wherein the controller is configured to determine the slope by determining a difference between a pair of consecutive sample points of the cardiac signal.

14. The device of claim 12, wherein the controller is configured to determine the slope by determining a sum of successive differences between consecutive sampling points.

15. The device of claim 12, wherein the controller is further configured to:
verify that the slope of the cardiac signal exceeded the short circuit threshold during a baseline portion of the cardiac signal, the baseline portion occurring between consecutive R-waves representative of ventricular depolarizations,
wherein the controller detects a short circuit event upon verifying that the slope of the cardiac signal exceeded the short circuit threshold during the baseline portion of the cardiac signal and does not detect a short circuit event upon not verifying that the slope of the cardiac signal exceeded the short circuit threshold during the baseline portion of the cardiac signal.

16. The device of claim 15, wherein the controller is further configured to:

determine at least one of (a) a difference between at least one pair of sample points that precede the samples used to determine the slope of the cardiac signal and (b) a sum of differences between a plurality of pairs of sample points preceding samples used to determine the slope of the cardiac signal; and verify that the slope of the cardiac signal exceeded the short circuit threshold during the baseline portion of the cardiac signal in response to either one of the difference being less than a baseline difference threshold and the sum being less than a baseline sum threshold.

17. The device of claim 12, wherein:

the sensing circuitry is configured to generate a cardiac sense event signal in response to sensing an R-wave from the cardiac signal;

the controller being further configured to:
  set a short circuit detection window having an onset spaced in time after the cardiac sense event signal is received from the sensing circuitry; and
  detect the short circuit event only during the short circuit detection window.

18. The device of claim 12, wherein the controller is further configured to verify the slope is a leading edge of a signal peak occurring during a baseline portion of the cardiac signal, the baseline portion occurring between consecutive R-waves representative of ventricular depolarizations.

19. The device of claim 12, wherein the controller is further configured to detect the short circuit event by:
  determining a trailing edge slope of the cardiac signal occurring during a baseline portion of the cardiac signal, the baseline portion occurring between R-waves representative of ventricular depolarizations,
  comparing the trailing edge slope to the slope that exceeds the short circuit threshold; and
  detecting the short circuit event in response to the trailing edge slope being less than the slope that exceeds the short circuit threshold and the trailing edge slope occurring after the slope that exceeds the short circuit threshold.

20. The device of claim 12, wherein the controller is further configured to perform an action comprising at least one of generate an alert signal in response to detecting the short circuit event and adjust a therapy delivery pathway in response to detecting the short circuit event.

* * * * *